Figure 1:
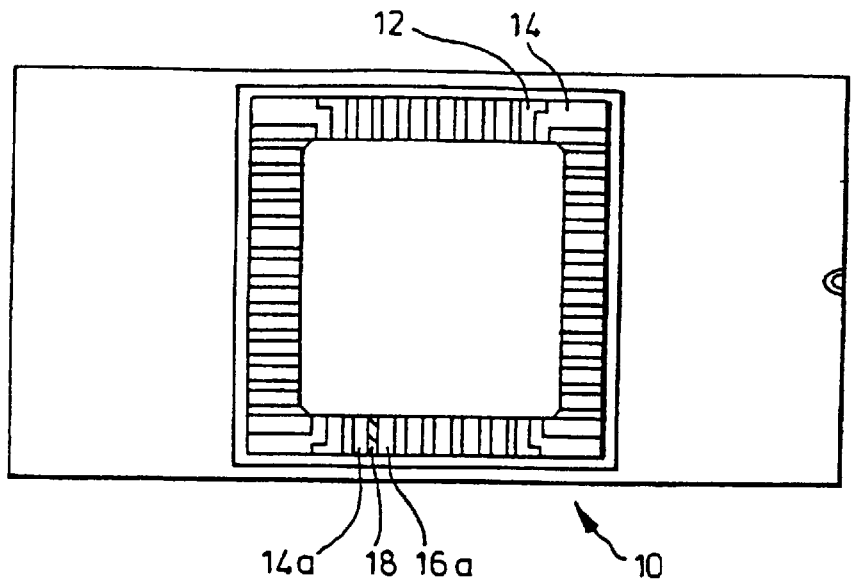

United States Patent
Persaud et al.

[11] Patent Number: 6,033,601
[45] Date of Patent: Mar. 7, 2000

[54] SEMICONDUCTING ORGANIC POLYMERS

[75] Inventors: Krishna Chandra Persaud, Charlton; Soad Mohialdin-Khaffaf, Whalley Range, both of United Kingdom

[73] Assignee: AromaScan plc, United Kingdom

[21] Appl. No.: 08/860,809

[22] PCT Filed: Dec. 4, 1995

[86] PCT No.: PCT/GB95/02818

§ 371 Date: Sep. 12, 1997

§ 102(e) Date: Sep. 12, 1997

[87] PCT Pub. No.: WO96/18888

PCT Pub. Date: Jun. 20, 1996

[30] Foreign Application Priority Data

Dec. 14, 1994 [GB] United Kingdom .................... 9425207

[51] Int. Cl.[7] .............................. H01B 1/00; G01N 7/00; G01N 27/00; C08G 73/06
[52] U.S. Cl. .......................... 252/500; 73/31.06; 528/423
[58] Field of Search ........................... 252/500; 528/423; 73/31.06

[56] References Cited

U.S. PATENT DOCUMENTS

| 4,443,615 | 4/1984 | Matsuoka et al. ....................... 548/489 |
| 4,488,943 | 12/1984 | Skotheim ................................ 204/58.5 |
| 4,887,455 | 12/1989 | Payne et al. ............................. 73/27 R |
| 5,107,308 | 4/1992 | Koezuka et al. ............................ 357/8 |
| 5,436,167 | 7/1995 | Robillard ................................ 436/165 |

FOREIGN PATENT DOCUMENTS

| 022028 | 6/1980 | European Pat. Off. ........ G01N 27/12 |
| 60-223817 | 11/1985 | Japan .............................. C08G 61/12 |
| 203553 | 10/1988 | United Kingdom ........... G01N 27/12 |

OTHER PUBLICATIONS

B.A. Gregory, "An Introduction to Electrical Instrumentation and Measurement Systems", pp. 215 and 220–221.

J.J. Miasik et al., "Conducting Polymer Gas Sensors", J. Chem. Soc., Faraday Trans. 1, 1986, pp. 1117–1126.

R. Waltman et al., "Substituent Effects in the Electropolymerization of Aromatic Heterocyclic Compounds", 1984, pp. 4343–4346.

*Primary Examiner*—Mark Kopec
*Assistant Examiner*—John M. Petruncio
*Attorney, Agent, or Firm*—Christie, Parker & Hale, LLP

[57] ABSTRACT

There is disclosed a semiconducting organic polymer polymerized from a 1-substituted, 3-substituted or 1,3-substituted indole monomer and a gas sensor containing this polymer as the active gas sensing element.

13 Claims, 10 Drawing Sheets

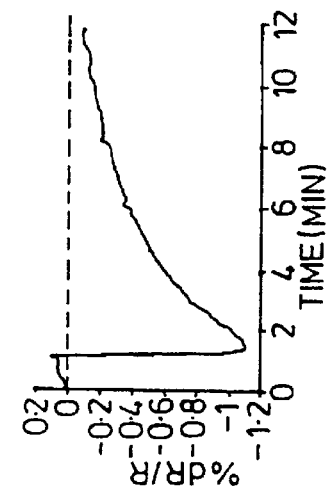
FIG. 6A POLY 3-HEXANOYLINDOLE RESPONSE TO PROPANOIC ACID
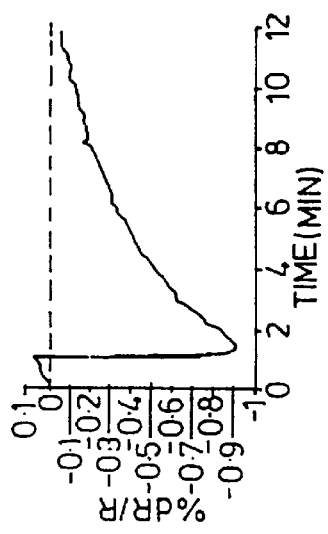
FIG. 6B POLY 3-DODECANOYLINDOLE RESPONSE TO PROPANOIC ACID
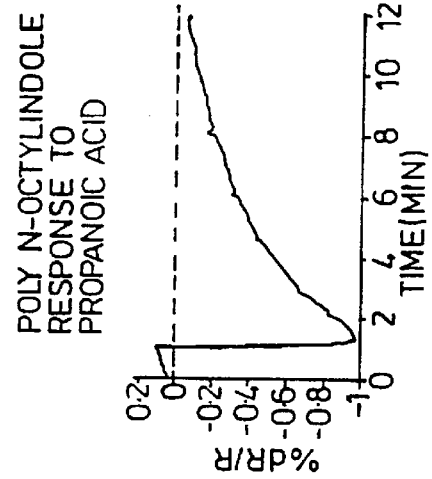
FIG. 6C POLY N-BENZYLINDOLE RESPONSE TO PROPANOIC ACID
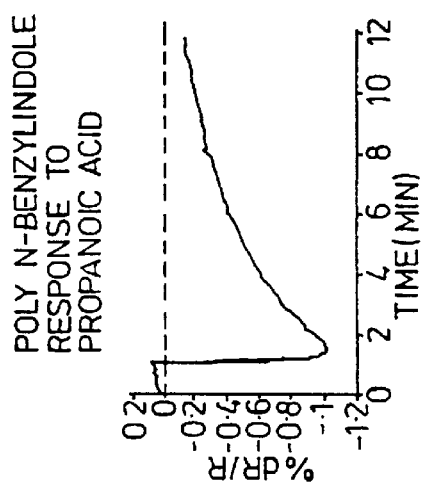
FIG. 6D POLY N-OCTYLINDOLE RESPONSE TO PROPANOIC ACID

POLY 3-DODECANOYLINDOLE RESPONSE TO BUTYRIC ACID

POLY N-OCTYLINDOLE RESPONSE TO BUTYRIC ACID

POLY 3-HEXANOYLINDOLE RESPONSE TO BUTYRIC ACID

POLY N-BENZYLINDOLE RESPONSE TO BUTYRIC ACID

POLY 3-HEXANOYLINDOLE
RESPONSE TO
VALERIC ACID

POLY 3-DODECANOYLINDOLE
RESPONSE TO
VALERIC ACID

POLY N-BENZYLINDOLE
RESPONSE TO
VALERIC ACID

POLY N-OCTYLINDOLE
RESPONSE TO
VALERIC ACID

POLY 3-HEXANOYLINDOLE RESPONSE TO PHENOL

POLY 3-DODECANOYLINDOLE RESPONSE TO PHENOL

POLY N-BENZYLINDOLE RESPONSE TO PHENOL

POLY N-OCTYLINDOLE RESPONSE TO PHENOL

SEMICONDUCTING ORGANIC POLYMERS

This invention relates to semiconducting organic polymers which may be used in gas sensors.

It is known that certain electrochemically prepared semiconducting polymers such as polypyrrole may be employed in sensors in order to detect gases, vapours and odours. Such a sensor may comprise a pair of electrodes mounted on a substrate, with a layer of the semiconducting organic polymer deposited on and between the electrodes in order to produce an electrical connection between the electrodes. The semiconducting organic polymer may be sensitive to the presence of a gas or, more likely, to a range of gases, to the extent that adsorption of the gas onto the polymer surface affects the physical and electrical properties of the polymer. Hence the presence of gas may be detected by monitoring, for example, the change in DC resistance of the sensor on exposure to the gas. For instance, Miasik et al (Miasik, J J, Hooper, A and Tofield, B C) J C S Faraday Trans. 1, 1986, 82, 1117–26 demonstrated a polypyrrole gas sensor displaying a DC resistance which was sensitive to the presence of nitrous oxide and hydrogen sulphide. GB-2, 203, 553-B discloses an improved method of detection wherein various AC impedance characteristics are measured at different AC frequencies.

A given semiconducting organic polymer will typically be sensitive to a range of compounds. Clearly this lack of selectivity is a major problem if one wishes to develop a sensor which is specific to a particular gas. Conversely, a sensor which employs a given semiconducting organic polymer will not be sufficiently sensitive to such a broad range of gases that it may be considered a general purpose device.

A solution to these problems is a device which employs a plurality of sensors, wherein each sensor incorporates a different polymer and each polymer possesses differing gas response profiles. Thus a suite of polymers may be selected which possess broadly overlapping responses, but which are individually chemically tailored to enhance differences in response to certain molecules or classes of molecules. Often the variation of a substituent group on the monomer unit is sufficient to enable such "fine tuning" of response. A multi-sensor device detects gases and odours as a characteristic pattern of individual responses across the array of sensors.

The present invention relates to a class of semiconducting organic polymers based on 1-substituted, 3-substituted and 1,3 substituted indole monomer units which display high sensitivity towards a number of important species.

According to a first aspect of the invention there is provided a semiconducting organic polymer polymerised from a 3-substituted or 1,3-substituted indole monomer.

According to a second aspect of the invention there is provided a semiconducting organic polymer polymerised from a 1-substituted, 3-substituted or 1,3-substituted indole monomer for use in a gas sensor.

A substituent at the 3 position may be an alkyl or aromatic acetyl group.

A substituent at the 1 position may be an alkyl group.

Alternatively, a substituent at the 1 position may contain an aromatic group. Said substituent may be tosyl or benzyl.

The substituted indole monomer may be polymerised electrochemically from a solution containing said monomer and a counter-ion. The counter-ion may be $BF_4^-$, $PF_6^-$, $ClO_4^-$, $C_8H_{17}SO_3^-$,$[Fe(CN)_6]^{3-}$ or $CH_3C_6H_4SO_3^-$.

The semiconducting organic polymer may be polymerised from a monomer selected from the group comprising: 1-octylindole; 1-benzylindole; 1-tosylindole; 1-tosylindole; 3-hexanoxyl-1-tosylindole; 3-hexanoylindole; 3-hexylindole; 3-dodecanoyl-1-tosylindole; 3-dodecanoylindole and 3-dodecylindole.

According to a third aspect of the invention there is provided a gas sensor comprising:
 a pair of electrodes;
 one or more semiconducting organic polymers, of which at least one is polymerised according to the first aspect of the invention, deposited between the pair of electrodes in such manner as to effect a semiconducting electrical connection between said electrodes;
 means for applying electric signal across the electrodes; and
 detection means for detecting a chosen electrical property in the presence of a gas.

Figure 2:
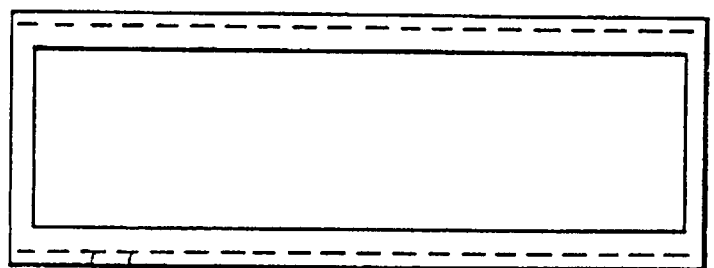
Figure 3:
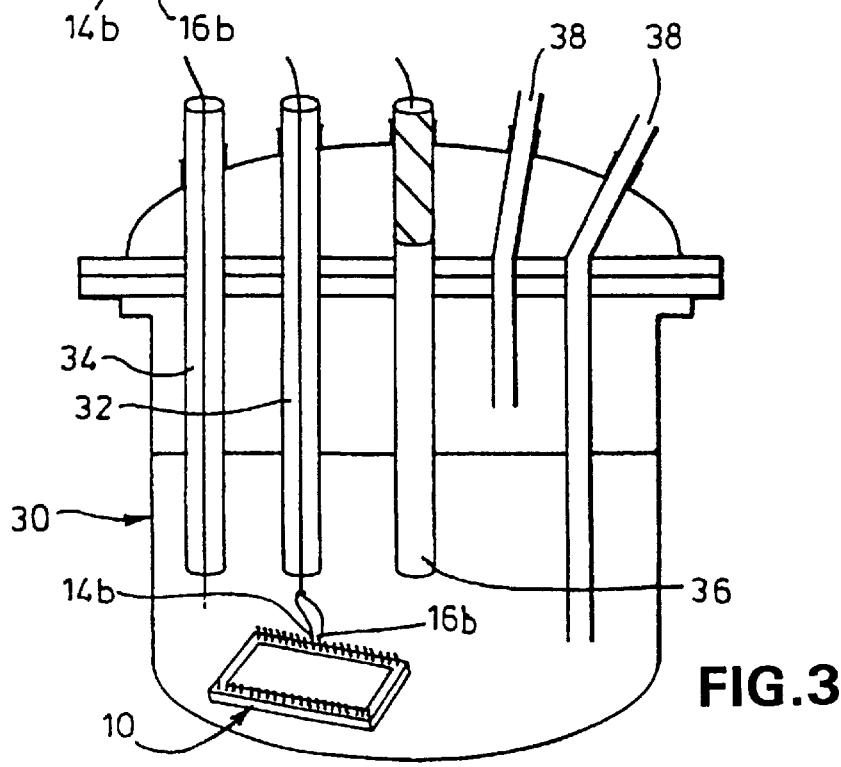
Figure 4:
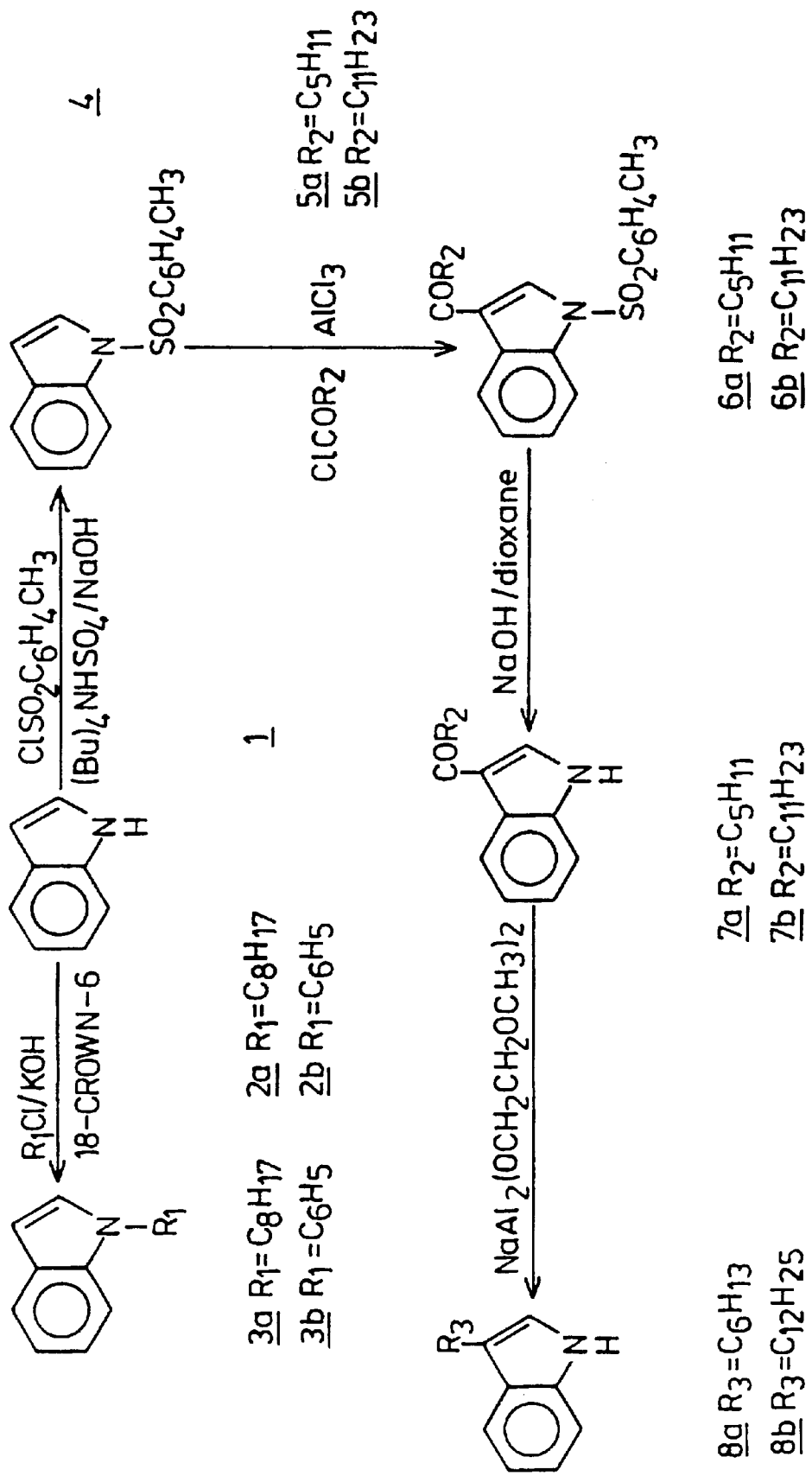
Figure 5A:
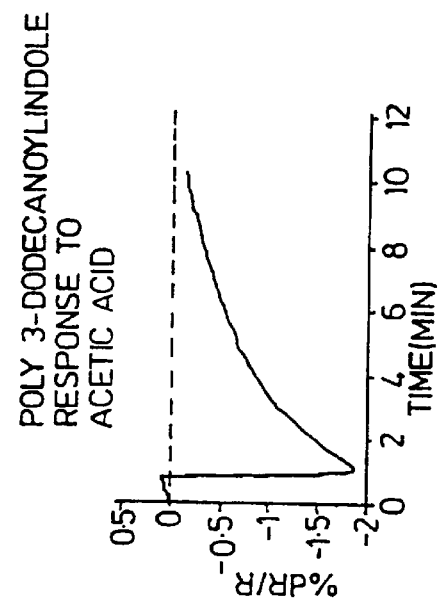
Figure 5B:
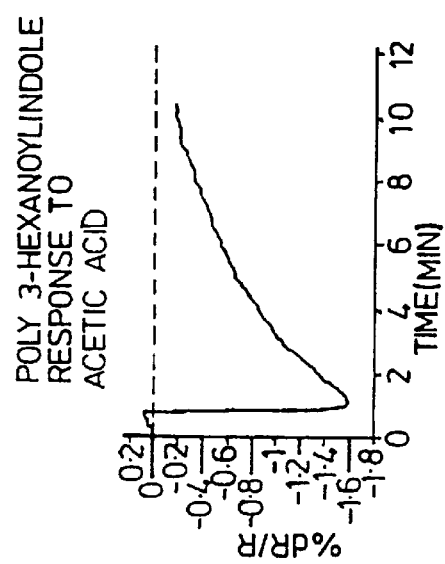
Figure 5C:
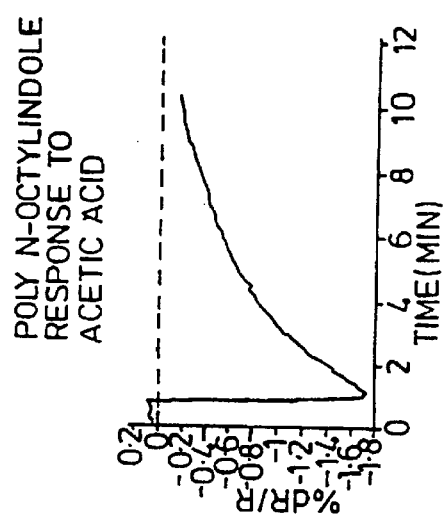
Figure 5D:
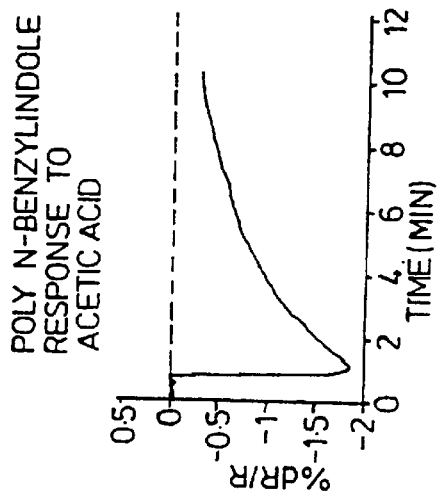
Figure 7B:
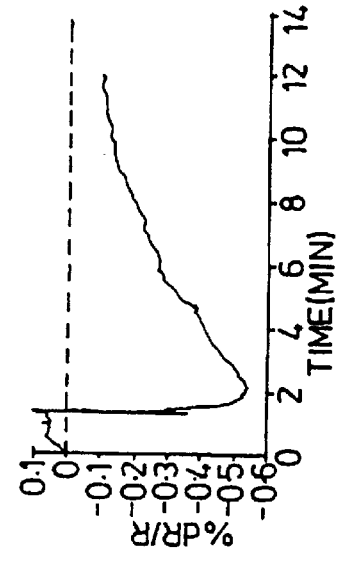
Figure 7D:
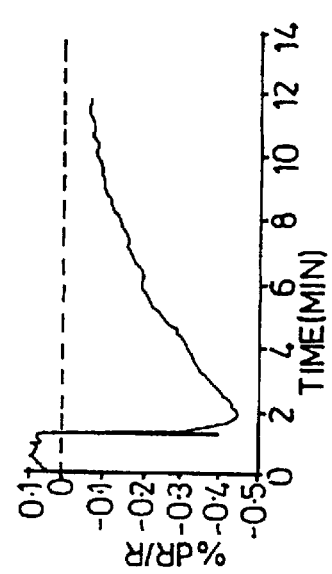
Figure 7A:
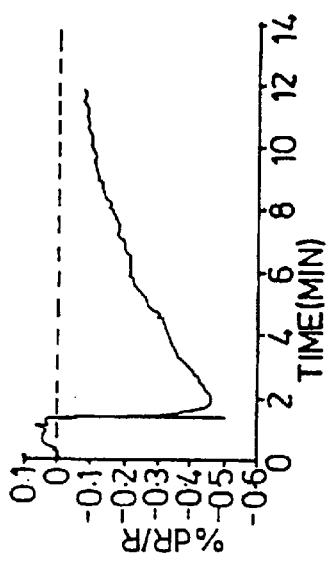
Figure 7C:
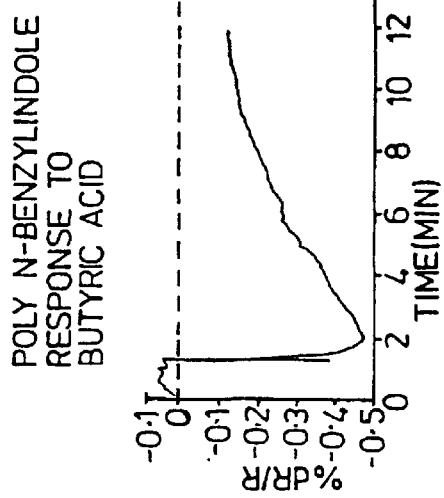
Figure 8A:
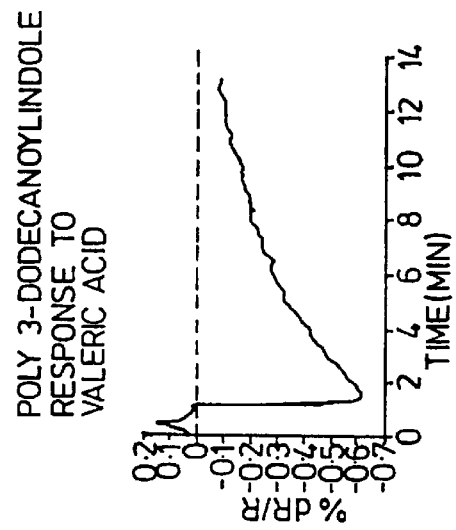
Figure 8B:
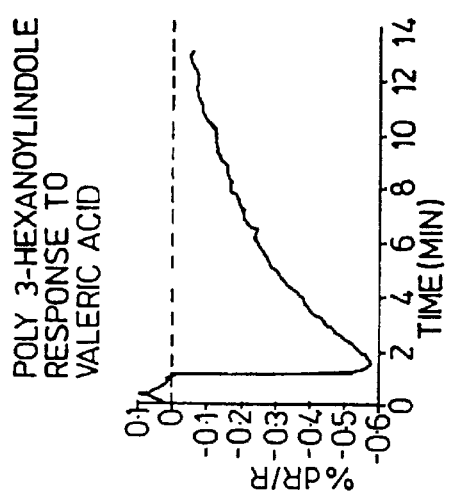
Figure 8C:
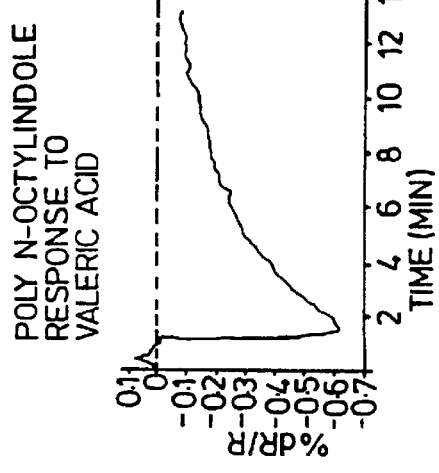
Figure 8D:
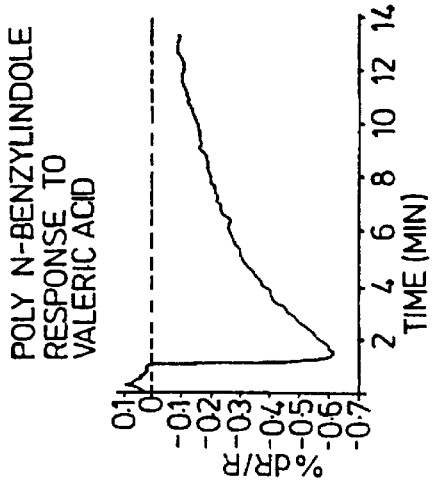
Figure 9A:
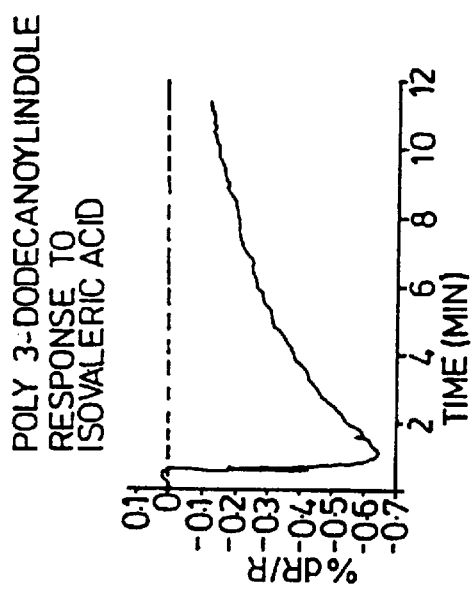
Figure 9B:
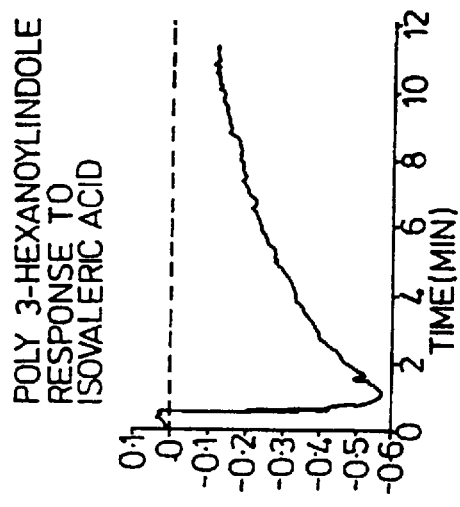
Figure 9C:
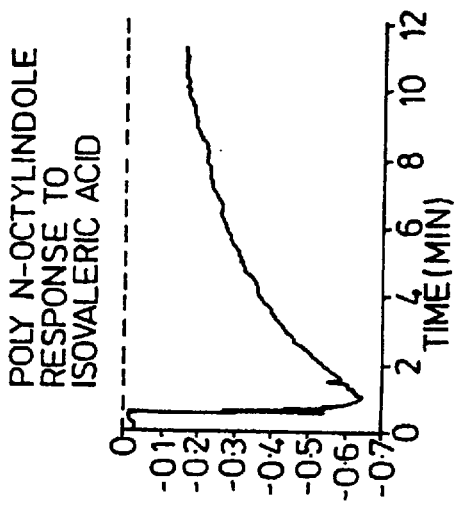
Figure 9D:
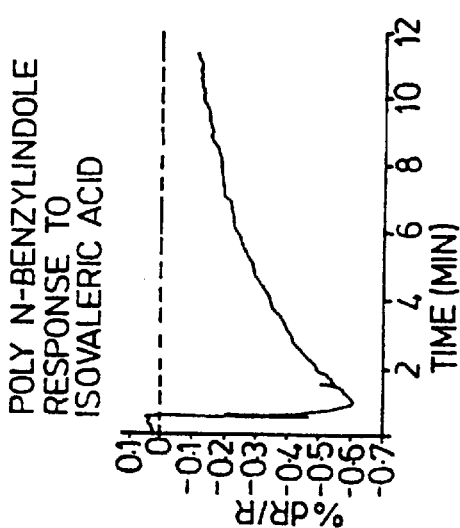
Figure 10A:
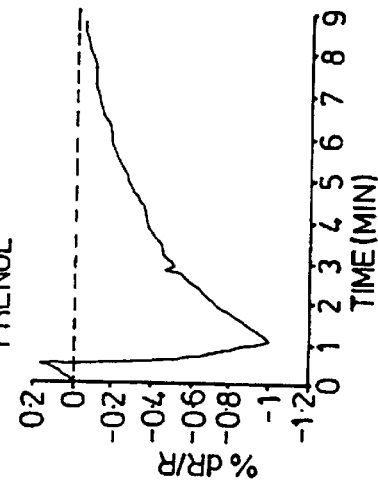
Figure 10B:
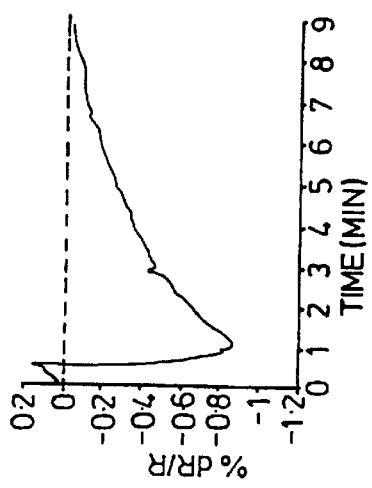
Figure 10C:
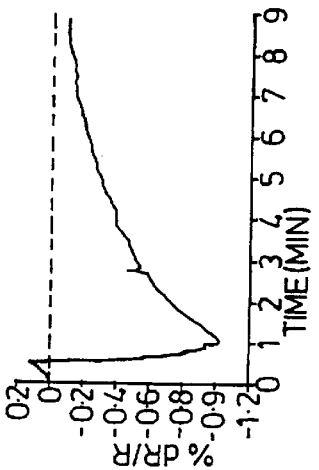
Figure 10D:
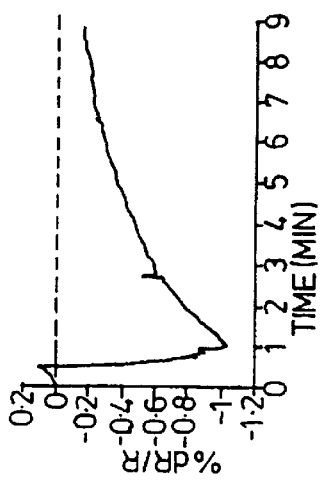
Figure 11A:
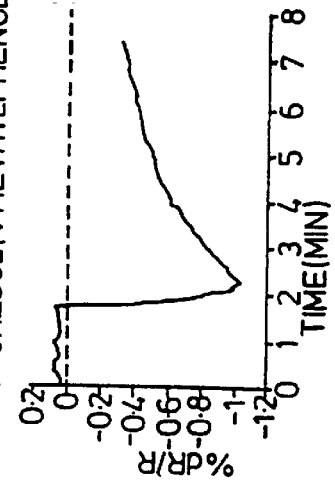
Figure 11B:
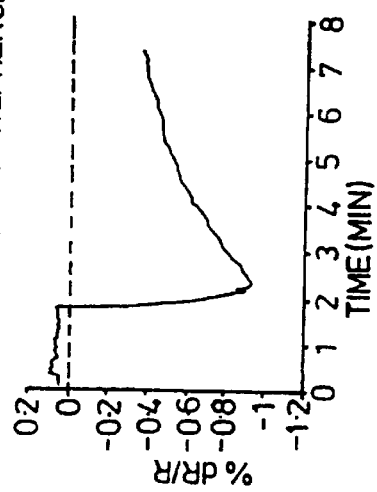
Figure 11C:
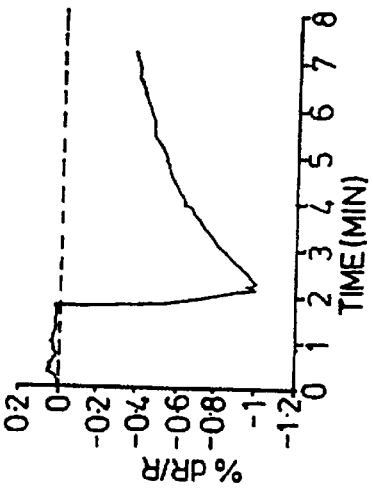
Figure 11D:
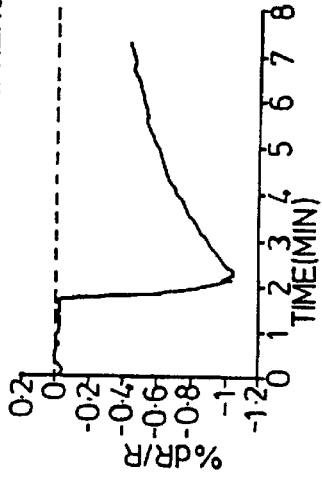
Figure 12A:
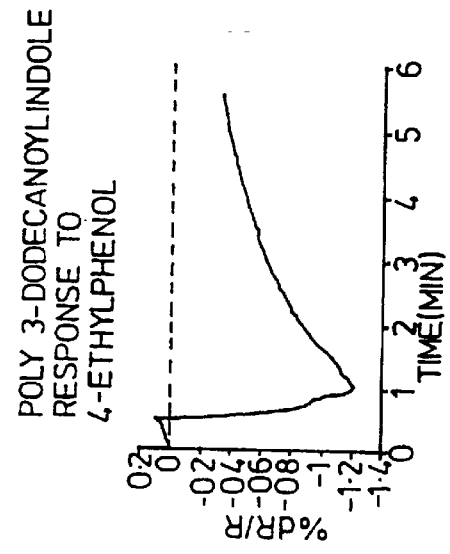
Figure 12B:
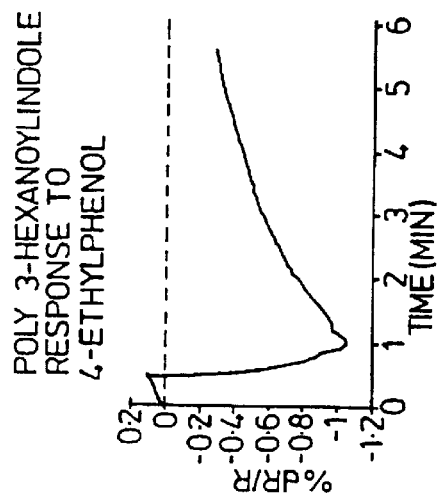
Figure 12C:
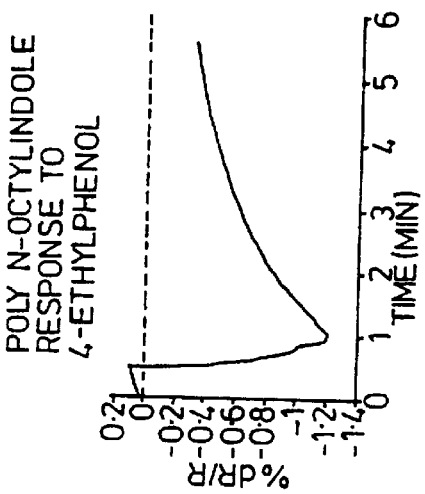
Figure 12D:
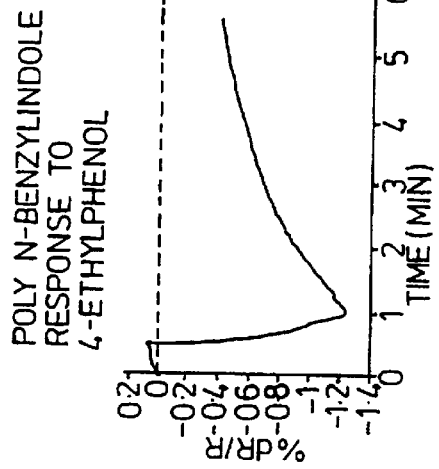

Semiconducting organic polymers in accordance with the invention will now be described with reference to the accompanying drawings in which:
 FIG. 1 shows a plan view of a gas sensor;
 FIG. 2 shows the view from below the gas sensor;
 FIG. 3 shows the electrochemical polymerisation process;
 FIG. 4 shows reaction schemes for the synthesis of substituted indoles;
 FIGS. 5A–5D shows the response of some polymers to acetic acid;
 FIGS. 6A–6D shows the response of some polymers to propanoic acid;
 FIGS. 7A–7D shows the response of some polymers to butyric acid;
 FIGS. 8A–8D shows the response of some polymers to valeric acid;
 FIGS. 9A–9D shows the response of some polymers to isovaleric acid;
 FIGS. 10A–10D shows the response of some polymers to phenol;
 FIGS. 11A–11D shows the response of some polymers to p-cresol; and
 FIGS. 12A–12D shows the response of some polymers to 4-ethylphenol.

Semiconducting organic polymers may be produced by the polymerisation of 1-substituted, 3-substituted and 1,3-substituted indole monomers. Such polymers are particularly useful in the manufacture of gas sensing devices of the type described hereinbefore, because as a class they exhibit high sensitivity towards important species such as thiols and phenols. These sensitivities can be one to two orders of magnitude greater than those displayed by the polyprrole based sensors commonly employed in the art. By judicious variation of substituent groups the polymer can be further "fine tuned" to respond more selectively with respect to the functional groups present in the detected molecule, or to molecular size and shape.

The substituent at the 3 position may be an alkyl or acetyl group. In particular, large (possessing 6 or more carbon atoms), bulky substituent groups confer greater selectivity on the resulting polymer, since steric considerations dictate that molecules must be of a certain size and/or shape in order to adsorb onto the surface of the polymer.

The substituent at the 1 position may also be alkyl, and a similar rationale indicates that this alkyl group is preferably large.

Alternatively, substituents at the 1 position may contain an aromatic group. For example, benzyl or tosyl substituents may be employed.

It will be appreciated that the foregoing discussion is not intended to be limiting in scope, and that other types of substituent groups, for example, a 3-substitutent containing an aromatic group, may be advantageously employed in accordance with the present invention. Similarly, it is not intended to limit the scope of the invention to gas sensor devices; polymers of the present invention may have application in any field known to employ semiconducting organic polymers.

FIG. 1 shows one embodiment of a gas sensor based on a modified 40 pin silicon chip carrier 10 (Hybritek 40 L CC), wherein the gold pins 12 of the carrier are patterned onto a ceramic substrate 14. Adjacent pins 14(a) and 16a act as electrodes, and a layer of semiconducting organic polymer according to the present invention 18 is deposited so that there is a semiconducting electrical connection between the electrodes. The electrodes are connected to plugs 14b and 16b, located on the underside of the chip carrier. Leads are attached to the plugs 14b and 16b in order to apply a DC potential across the electrodes and the resistance of this electrical circuit is measured by known means (see, for example, B A Gregory; "An Introduction to Electrical Instrumentation and Measurement Systems", 1982, MacMillen.) When the sensor is exposed to a gas to which the polymer is sensitive, the presence of the gas is detected by a variation in the DC resistance of the circuit.

In order to produce the polymer in its conducting form an electrochemical polymerisation process is employed. The polymerisation may be carried out by electrolytic oxidation of the monomer in an electrochemical cell. FIG. 3 shows the electrolytic oxidation of 3-methyl indole in an electrochemical cell 30. The chip carrier 10 is connected, at 14b and 16b, to the anode 32 of the cell. The cell also comprises a cathode 34, a standard calomel reference electrode 36 and is flushed with nitrogen through ports 38. The anode is at 2 V with respect to the reference electrode 36. The electrolyte comprises 0.1M of the monomer and 0.1M tetraethylammonium p-toluenesulphonate in a 99% acetonitrile/1% water medium.

In solution the tetraethylammonium p-toluenesulphonate yields the tosylate anion, which is incorporated into the polymer film during polymerisation as a counter-ion to ensure overall electrical neutrality in the polymer. Other counter-ions may be employed including, for example, $BF_4^-$, $PF_6^-$, $ClO_4^-$, $C_8H_{17}SO_3^-$ or $[Fe(CN)_6]^{3-}$. Variation of the counter-ion is another means by which the response characteristics of a polymer may be moderated.

FIG. 4 shows reaction schemes for the synthesis of nine substituted indole monomers. The reactions are described in more detail below. All nmr data is reported in ppm and recorded at 300 MHz.

Preparation of 1-octylindole (3a)

A mixture of indole (1) (0.03 mole, 3.51 g), potassium hydroxide (0.03 mole, 1.97 g) powdered in a mortar, and 18-crown-6 ether (0.001 mole, 250 mg) in benzene (20 cm$^3$) is heated under reflux with vigorous stirring for two hours. A solution of octylbromide (2a), (0.04 mole, 7.72 g) in benzene (10 cm$^3$) is added and reflux is maintained for an additional four hours. The reaction is monitored by TLC and the reaction mixture is filtered on Celite. Evaporation of the solvent yields an orange liquid which is purified by distillation in vacuo. The colourless liquid distilled at 154–156° C. and 1.5 mmHg pressure is shown by $^1$H nmr to be pure 1-octylindole (3a) (4.98 g, 0.0217 mole, 72% yield).

[Found; C,83.5; H,10.2; N,6.4%: Calc. for $C_{16}H_{23}N$; C,83.8, H, 10.04; N, 6.1%]

$^1$H nmr (in CDCl$_3$): 1.0 (t,3H); 1.37 (m, 10H); 1.88(m, 2H); 4.13(t,2H); 6.59 (d,1H); 7.12(d,1H); 7.2(t,1H); 7.3 (t,1H); 7.42(d,1H); 7.75 (d, 1H)

Preparation of 1-benzylindole (3b)

A mixture of indole (1) (0.03 mole, 3.51 g), potassium hydroxide (0.03 mole, 1.97 g)) powdered in a mortar and 18-crown-6 ether (0.001 mole, 250 mg) in benzene (20 cm$^3$) is heated under reflux with vigorous stirring for two hours. A solution of benzyl chloride (26) (0.04 mole, 5.06 g) in benzene (10 cm$^3$) is added to the above mixture and reflux is maintained for an additional four hours. The reaction is monitored by TLC. The reaction mixture is filtered on Celite. Evaporation of the solvent gives an orange liquid which is purified by dry column chromatography eluted using a mixture of dichloromethane in 50% petroleum ether. Evaporation of the solvent gives a colourless thick liquid which is solidified in the presence of diethyl ether to give a white solid of 1-benzylindole (3b) (1.2 g, 0.007 mole, 25%), m.p. 48–51° C., shown to be pure by $^1$H nmr.

[Found; C, 86.6; H, 6.4; N, 6.8%: Calc. for $C_{15}H_{13}N$; C,86.9; H,6.28; N, 6.76%]

$^1$H nmr (in CDCl$_3$/TMS): 5.2 (s, 2H); 5.41 (d,1H); 6.93–7.2 (complex, 9Ar-H), 7.55 (d.d, 1H)

Preparation of 1-tosylindole (4)

A mixture of indole (1) (0.157 mole, 18.4 g), dichloromethane (100 cm$^3$), tetrabutylammonium hydrogen sulphate (0.016 mole, 5.3 g) and sodium hydroxide solution (128 cm$^3$, 50% aqueous) is made in 3-necked flask (500 cm$^3$). The stirred mixture is cooled in water and p-toluenesulfonyl chloride (45.7 g, 0.24 mole) in dichloromethane (20 cm$^3$) is added fairly rapidly so that the mixture refluxes gently. When the addition is complete the mixture is stirred at room temperature for a further 20 hours.

The inorganic precipitate is collected on Celite by suction filtration. The organic layer is separated using a separating funnel, washed five times with water, and dried over anhydrous magnesium sulphate (MgSO$_4$). The aqueous layer is diluted with an equal volume of water and then extracted with dichloromethane. The dichloromethane extracts are washed with water, combined with the organic material, then dried over anhydrous magnesium sulphate. Evaporation of the solvent gives a thick oil, which is crystallised from dichloromethane and hexane to give pinkish crystals. Recrystallisation from dichloromethane and hexane affords cream white crystals of 1-tosylindole (4) (32.3 g, 0.119 mole, 76%), m.p. 74–76° C.

[Found; C, 66.2; H,4.5; N, 5.0; S,12.0: Calc. for $C_{15}H_{13}NSO_2$; C,66.4; H,4.7; N,5.2; S,11.8]

$^1$H nmr (in CDCl$_3$/TMS): 2.21 (S, 3H), 6.55 (d, 1H), 7.05–7.25 (m, 4H, Ar), 7.45 (d.d, 1H), 7.7 (d.d, 1H), 7.9 (d,1H)

Preparation of 3-hexanoyl-1-tosylindole (6a)

Aluminium trichloride (6.01 g, 45.2 mmol), is suspended in dichloromethane (80 cm$^3$), under nitrogen. A solution of hexanoyl chloride (5a) (6.62 g, 49.2 mmol) in dichloromethane (20 cm$^3$) is added slowly to the stirred mixture at ambient temperature. After the addition is complete, the mixture is stirred for a further 10 minutes. The reaction mixture is cooled to 5° C. 1-tosylindole (4) (45.2 mmol, 12.24 g) in dichloromethane (20 cm$^3$) is added to the mixture while the temperature is maintained at 5° C. After two hours stirring at room temperature the reaction mixture is treated with ice water, extracted with dichloromethane and dried over magnesium sulphate. Evaporation of the solvent gives a thick oil, which crystallises in the presence of methanol and dichloromethane to yield colourless crystals of 3-hexanoyl-1-tosylindole (6a) (13.07 g, 35.42 mmol, 78%), m.p. 91–93° C.

[Found: C, 68.1; H, 6.1; N,3.8; S, 8.5: Calc. for $C_{21}H_{23}NSO_3$; C, 68.3; H, 6.2; N,3.8; S,8.6]

$^1$H nmr (in CDCl$_3$/TMS): 0.93 (t,3H); 1.38(m,4H); 1.76 (m,2H); 2.36 (s,3H,Me in Ts); 2.86 (t,2H); 7.25 (d,2H Ar in Ts); 7.35 (M, 2H in indole); 7.81 (d, 2H Ar in Ts); 7.92 (dm, 1H), 8.21 (s, 1H in indole), 8.35 (dm, 1H in indole)

Preparation of 3-hexanoylindole (7a)

3-hexanoyl-1-tosylindole (6a) (3.96 g, 10 mmol) is dissolved in dioxane (60 cm$^3$). Sodium hydroxide (5M, 60 cm$^3$) is added to the solution which is stirred under reflux for 24 hours. The organic phase is separated from the aqueous layer by extraction with diethyl ether. The combined extracts are washed with saturated sodium chloride solution and dried over anhydrous MgSO$_4$. Evaporation of the solvent gives a white solid which is recrystallised from methanol and diethyl ether to give white crystals, identified by $^1$H nmr as 3-hexanoylindole (7a) (1.72 g, 8 mmol, 80%), m.p. 153–154° C.

[Found; C,78.4; H, 8.1; N,6.5: Calc. for C$_{14}$H$_{17}$NO; C, 78.14; H, 7.9; N,6.5]

$^1$H nmr (in CDCl$_3$/DMSO d$_6$): 0.85 (t,3H), 1.32(m,4H), 1.7 (m,2H), 2.8 (t,2H), 7.18(m,2H); 7.38 (dm, 1H), 7.82 (d, 1H), 8.3 (dm, 1H), 10.93 (bs, N-H)

Preparation of 3-hexylindole (8a)

Red-Al [NaAlH$_2$(OCH$_2$CH$_2$OCH$_3$)$_2$] (11.3 g, 3.4M in toluene), is dissolved in benzene (50 cm$^3$), and suspended under nitrogen. 3-hexanoylindole (7a) (5.59 g, 26 mmol) in benzene (30 cm$^3$) is added in a drop-wise manner at 0° C. (zero)(ice cooled), and extra benzene (20 cm$^3$) is added later on. The reaction mixture is stirred at room temperature for three hours and at 50° C. for one hour. The reaction mixture is then cooled to room temperature and cautiously hydrolysed with 100 cm$^3$ of water. The white precipitate is removed by filtration. The organic layer is extracted using diethyl ether (5× 25 cm$^3$), and dried over MgSO$_4$. Evaporation of the solvent yields thick green liquid which was purified by dry column flash chromatography. The thick yellow liquid is distilled fractionally under vacuum and the pure product distilled at 146° C., 1.5 mmHg. This was shown by $^1$H nmr to be pure 3-hexylindole (8a) (3.15 g, 15.7 mmol, 70%).

[Found; C, 83.3; H, 9.8; N, 7.3: Calc. for C$_{14}$H$_{19}$N; C,83.5; H, 9.5; N, 7.0]

$^1$H nmr (in CDCl$_3$): 1.02 (t, 3H), 1.4 (m, 6H), 1.8 (quintet, 2H), 2.85 (t,2H), 6.92 (s, 1H), 7.18–7.38 (m, 3H), 7.65 (bs, N-H), 7.7 (d, 1H).

Preparation of 3-dodecanoyl-1-tosylindole (6b)

A solution of dodecanoyl chloride (5b) (5.37 g, 24.6 mmol) in dichloromethane (20 cm$^3$) is added slowly to a suspension of aluminium chloride (3.0 g, 22.6 mmol) in dichloromethane (40 cm$^3$) under N$_2$. After the addition is complete the mixture is stirred for ten minutes, then 1-tosylindole (4) (6.12 g, 22.6 mmol) in dichloromethane (20 cm$^3$) is added at 5° C. After two hours stirring at room temperature, the reaction mixture is treated with ice water. The organic layer is extracted with dichloromethane and dried over anyhdrous MgSO$_4$. Evaporation of the solvent gives a thick orange liquid which crystallises to a white solid when treated with a mixture of methanol and dichloromethane. This is filtered off and dried in vacuo, and is shown by $^1$H nmr to be a pure product of 3-dodecanoyl-1-tosylindole (6b) (9.0 g, 19.8 mmol, 87.7%), m.p. 79–80° C.

Found: C, 71.2; H, 7.5; N, 2.9; S, 7.4: Calc. for C$_{27}$H$_{35}$NSO$_3$; C,71.5, H, 7.7; N, 3.1; S, 7.1;)

$^1$H nmr (in CDCl$_3$): 0.88 (t, 3H), 1.3 (m, 16H), 1.77 (quintet, 2H), 2.35 (s, 3H), 2.89 (t, 2H), 7.28 (d, 2H, Ar), 7.35 (m,2H), 7.83 (d,2H), 7.93 (dm, 1H), 8.22 (s, 1H), 8.35 (dm, 1H)

Preparation of 3-dodecanoylindole (7b)

3-dodecanoyl-1-tosylindole (6b) (6.7 g, 15 mmol) is dissolved in dioxane (90 cm$^3$). Sodium hydroxide (5M, 90 cm$^3$) is added to the solution, which is stirred under reflux for 24 hours. The organic phase is separated from the aqueous layer by extraction with diethyl ether. The combined extracts are washed with saturated sodium chloride solution, and dried over anhydrous MgSO$_4$. Evaporation of the solvent yields a white solid which is recrystallised from methanol and diethyl ether to give white crystals, identified by $^1$H nmr as 3-dodecanoylindole (7b) (3.94 g, 13.2 mmol, 88%), m.p. 129–130° C.

[Found: C, 80.4; H, 9.9: N, 4.7: Calc for C$_{20}$H$_{29}$NO; C,80.3: H,9.6; N, 4.7.]

$^1$H nmr (in CDCl$_3$/DMSO d$_6$): 0.46 (t,3H); 0.9 (m,10H); 1.35 (quintet, 2H); 2.42 (t,2H); 6.81(m,2H); 7.08(d,m,1H); 7.5(d, 2H); 7.9(dm, 2H); 10.93 (bs, N-H).

Preparation of 3-dodecylindole (8b)

Red-Al[NaAlH2 (OCH2CH2OCH3)$_2$] (6.78 g, 3.4M in toluene) is dissolved in dry benzene (40 cm$^3$), and is suspended under nitrogen. 3-dodecanoylindole (7b) (4.2 g, 14 mmol) in benzene (30cm$^3$) is added in a drop-wise manner at 0° C. (ice cooled), and extra benzene (20cm$^3$) is added later on. The reaction mixture is stirred at room temperature for 3 hours, and at 50° C. for 1 hour. The reaction mixture is then cooled to room temperature and cautiously hydrolysed using 100 cm$^3$ water. The white precipitate is removed by filtration. The organic layer is extracted using diethyl ether (5×25 cm$^3$), and dried over MgSO$_4$. Evaporation of the solvent yields a thick green liquid which is purified by dry column flash chromatography (using a solvent mixture of 50% dichloromethane in petroleum ether b.p. 30–40° C.). Evaporation of the solvents gives a white solid, which is shown by $^1$H nmr to be pure 3-dodecylindole (8b) (2.65 g, 9.19 mmol, 65%)

[Found: C,84.1, H,11.2; N,5.1: Calc. for C$_{20}$H$_{31}$N; C,84.2; H, 10.9; N,4.9]

$^1$H nmr (in CDCl$_3$): 0.85 (t,3H); 1.25(m, 10H); 1.7 (quintet, 2H); 2,7 (t,2H); 6.96 (s,1H); 7.1–7.2 (m,2HAr); 7.35 (d,1H); 7.6 (d,1H); 7.9(bs, N-H)

Gas sensors were fabricated using poly 3-hexanoylindole, poly 3-dodecanoylindole, poly N-benzylindole and poly N-octylindole as the active gas sensing elements. The sensors were exposed to pulses of saturated vapour of the compounds listed in Table 1 at room temperature. The responses of the polymers were detected by monitoring the change in DC resistance of the sensor on exposure to vapour.

TABLE 1

Compounds detected by the gas sensors.

| Compound | Saturated Vapour Pressure/mmHg (at 25° C.) | Concentration/ppm (at 25° C.) |
|---|---|---|
| acetic acid | 14.4 | 20235 |
| propanoic acid | 3.9 | 4902 |
| butyric acid | 0.78 | 85.5 |
| valeric acid | 0.21 | 36.48 |
| isovaleric acid | 0.35 | 0.998 |
| phenol | 0.45 | 461.7 |
| p-cresol | 0.22 | 114 |
| 4-ethylphenol | 0.06 | 74.1 |

The responses of the various polymers are shown in FIGS. 5–12 and indicate that the polymers are sensitive to a range of compounds, including a number of phenols.

We claim:

1. A semiconducting organic polymer polymerised from a 3-substituted or 1,3-substituted indole monomer.

2. A semiconducting organic polymer polymerised from a 1-substituted, 3-substituted or 1,3-substituted indole monomer for use in a gas sensor.

3. A semiconducting organic polymer according to claim 1 or claim 2 wherein the substituent at the 3 position is an alkyl group.

4. A semiconducting organic polymer according to claim 1 or claim 2 wherein the substituent at the 3 position is an acetyl or an aromatic group.

5. A semiconducting organic polymer according to claim 1 or claim 2 in which the substituent at the 1 position is an alkyl group.

6. A semiconducting organic polymer according to claim 1 or claim 2 comprising an alkyl or acetyl substituent or substituents which substituent or substituents possesses at least six carbon atoms.

7. A semiconducting organic polymer according to claim 1 or claim 2 in which the substituent at the 1 position contains an aromatic group.

8. A semiconducting organic polymer according to claim 1 or claim 2 in which the substituent at the 1 position is benzyl.

9. A semiconducting organic polymer according to claim 1 or claim 2 in which the substituent at the 1 position is tosyl.

10. A semiconducting organic polymer according to claim 1 or claim 2 polymerised electrochemically from a solution containing the monomer and a counter-ion.

11. A semiconducting organic polymer according to claim 1 or claim 2 polymerised electrochemically from a solution containing the monomer and a counter-ion in which the counter-ion is selected from the group comprising $BF_4^-$, $PF_6^-$, $ClO_4^-$, $C_8H_{17}SO_3^-$, $[Fe(CN)_6]^{3-}$ or $CH_3C_6H_4SO_3^-$.

12. A semiconducting organic polymer according claim 1 or claim 2 in which the monomer is selected from the group comprising:

1-octylindole; 1-benzylindole; 1-tosylindole; 3-hexanoxyl-1-tosylindole; 3-hexanoylindole; 3-hexylindole; 3-dodecanoyl-1-tosylindole: 3-dodecanoylindole and 3-dodecylindole.

13. A gas sensor comprising:

a pair of electrodes;

one or more semiconducting organic polymers of which at least one is a semiconducting organic polymer according to claim 2 deposited between the pair of electrodes in such manner as to effect a semiconducting electrical connection between said electrodes;

means for applying electric signal across said electrodes; and detection means for detecting a chosen electrical property in the presence of a gas.

\* \* \* \* \*